(12) United States Patent
Garvey et al.

(10) Patent No.: US 11,065,042 B2
(45) Date of Patent: Jul. 20, 2021

(54) BONE PLATE AND GUIDE BLOCK AND ATTACHMENT MECHANISM THEREOF

(71) Applicant: Flower Orthopedics Corporation, Horsham, PA (US)

(72) Inventors: Brian Garvey, Media, PA (US); Tim Niacaris, Mansfield, TX (US)

(73) Assignee: Flower Orthopedics Corporation, Horsham, PA (US)

( * ) Notice: Subject to any disclaimer, the term of this patent is extended or adjusted under 35 U.S.C. 154(b) by 234 days.

(21) Appl. No.: 15/015,943

(22) Filed: Feb. 4, 2016

(65) Prior Publication Data
US 2016/0220286 A1 Aug. 4, 2016

Related U.S. Application Data

(60) Provisional application No. 62/111,890, filed on Feb. 4, 2015.

(51) Int. Cl.
| | |
|---|---|
| *A61B 17/17* | (2006.01) |
| *A61B 17/80* | (2006.01) |
| *A61B 50/30* | (2016.01) |

(52) U.S. Cl.
CPC .......... *A61B 17/80* (2013.01); *A61B 17/1728* (2013.01); *A61B 17/8061* (2013.01); *A61B 50/30* (2016.02)

(58) Field of Classification Search
CPC .......................... A61B 17/1728; A61B 17/80
See application file for complete search history.

(56) References Cited

U.S. PATENT DOCUMENTS

| | | | |
|---|---|---|---|
| 7,578,825 B2 | 8/2009 | Huebner | |
| 8,523,862 B2 | 9/2013 | Murashko, Jr. | |
| 9,050,151 B2 | 6/2015 | Schilter | |
| 2005/0085818 A1* | 4/2005 | Huebner | ............ A61B 17/1728 606/281 |
| 2005/0085824 A1* | 4/2005 | Castaneda | .......... A61B 17/1725 606/98 |
| 2011/0106086 A1 | 5/2011 | Laird | |

* cited by examiner

*Primary Examiner* — Olivia C Chang
(74) *Attorney, Agent, or Firm* — Ice Miller LLP (57) ABSTRACT

The present invention provides systems and devices for fixing the angle of instruments passing through a bone plate, as well as methods for using the same. The devices include bone plates and complementary guide blocks having features for secure attachment, as well as features for simple detachment.

13 Claims, 8 Drawing Sheets

BONE PLATE AND GUIDE BLOCK AND ATTACHMENT MECHANISM THEREOF

CROSS-REFERENCE TO RELATED APPLICATIONS

This application claims priority to U.S. Provisional Patent Application No. 62/111,890 filed Feb. 4, 2015, the contents of which are incorporated by reference herein in its entirety.

BACKGROUND OF THE INVENTION

Bone plates are used to provide stabilization between fragments of a fracture, joint, or osteotomy, allowing the fragments to heal through fusion. Bone plates are held in place with locking or non-locking screws and/or pegs. Anatomy specific plates may have predetermined screw bore trajectories that target specific anatomic landmarks or areas of particular clinical interest. When several screw bores are in relatively close proximity, a surgeon may prefer to use a guide block to facilitate pilot bore drilling. While guide blocks have been used in the past, current designs are cumbersome and do not provide features to ease the separation of guide block from bone plate.

U.S. Pat. No. 7,578,825 describes a guide device capable of being attached to a bone plate using a threaded coupling member. U.S. Pat. No. 8,523,862 describes a guide block and bone plate system wherein separate locking elements are provided to secure the guide block and bone plate. U.S. Pat. No. 9,050,151 describes an aiming device having extension that fit snugly into a bone plate and an additional 'joystick' for securing the aiming device to the bone plate. Introducing additional coupling members, locking elements, and joysticks complicates surgical procedures, and especially in U.S. Pat. No. 8,523,862, having locking elements occupy screw bores requires extra steps to maneuver around the locking elements when drilling and inserting screws.

U.S. patent application Ser. No. 12/936,195 describes a tool jig for use with a bone plate, wherein the tool jig comprises finger members that engage and clip onto the perimeter of the bone plate. While this system does not necessarily require additional elements, the attachment method has a larger footprint than the bone plate and may be difficult to attach in small spaces.

There is a need in the art for an improved bone plate and guide block system that simplifies attachment and detachment between the bone plate and guide block. The present invention meets this need.

SUMMARY OF THE INVENTION

In one aspect, the present invention relates to a bone plate and complementary guide block system, comprising: a bone plate comprising a rigid plate body, a plurality of bores therein, each bore having an angle of orientation, and at least one post bore; and a guide block comprising a rigid guide block body, a plurality of bores therein, each bore having an angle of orientation, and at least one post; wherein the at least one post seats within the at least one post bore to firmly attach the guide block to the bone plate with a friction, and wherein each of the plurality of guide block bores and each of the plurality of bone plate bores align such that the angle of orientation between each of the plurality of guide block bores and each of the plurality of bone plate bores is constant.

In one embodiment, the bone plate body comprises a polymer or a metal. In one embodiment, the guide block body comprises a polymer or a metal. In one embodiment, the at least one post comprises an at least partially deformable material. In one embodiment, at least one bone plate bore and at least one guide block bore is sized to fit a bone screw. In one embodiment, at least one bone plate bore and at least one guide block bore is sized to fit a Kirschner wire (K-wire). In one embodiment, at least one bone plate bore and at least one guide block bore is threaded. In one embodiment, the guide block comprises a lip to provide a gap between a guide block attached to a bone plate.

In one embodiment, at least one post bore is selected from the group consisting of: a straight post bore having a constant diameter throughout; a flared post bore having an increasing diameter from the top of the post bore to the bottom of the post bore; a tapered post bore having a decreasing diameter from the top of the post bore to the bottom of the post bore; a stepped post bore comprising at least two sections, each section having a different diameter; and a recessed post bore comprising at least two regions, wherein at least one region has a constant diameter and at least one region has a flared or a tapered diameter.

In one embodiment, at least one post is selected from the group consisting of: a straight post having a constant diameter throughout; a flared post having an increasing diameter extending away from the guide block; a tapered post having a decreasing diameter extending away from the guide block; a stepped post comprising at least two sections, each section having a different diameter; and a barbed post comprising at least two regions, wherein at least one region has a constant diameter and at least one region has a flared or a tapered diameter.

In one embodiment, at least one post is a pliant post comprising at least one cut splitting the post into at least two pliant elements, wherein the at least two pliant elements are reversibly deformable inwards to decrease the diameter of the pliant post and reversibly deformable outwards to increase the diameter of the pliant post. In one embodiment, the pliant post further comprises: an at least partially threaded expansion bore extending through the pliant post and the guide block body; and a guide block screw having a screw head and a screw shaft; wherein actuating the guide block screw within the expansion bore advances the screw shaft through the pliant post and reversibly deforms the pliant elements outwards to increase the diameter of the pliant post.

In one embodiment, the guide block further comprises: an at least partially threaded separation bore extending through the guide block body; and a guide block screw having a screw head and a screw shaft; wherein actuating the guide block screw within the separation bore advances the screw shaft through the guide block to contact and push away a bone plate attached to the guide block.

In another aspect, the invention relates to a method of detaching the guide block and the bone plate of the system of the present invention, the method comprising gripping and pulling the guide block from the bone plate.

In another aspect, the invention relates to a method of detaching the guide block and the bone plate of the system of the present invention, the method comprising inserting an instrument into a gap between the guide block and the bone plate and levering the guide block and the bone plate apart.

In another aspect, the invention relates to a method of detaching the guide block and the bone plate of the system of the present invention, the method comprising actuating the guide block screw within the separation bore until the screw shaft contacts and separates the bone plate from the guide block.

In another aspect, the invention relates to a sterile kit comprising at least one system of the present invention. In one embodiment, the kit further comprises one or more instruments selected from the group consisting of: an implantable screw, a screwdriver, a screw depth gauge, a K-wire, a guide wire, a drill bit, a drill guide, and a bone tap. In one embodiment, the one or more instruments are individually packaged in sterile packages. In one embodiment, the kit comprises instructional material.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 4A through FIG. 4E depict a plurality of bone plate post bore designs.

FIG. 5A through FIG. 5E depict a plurality of guide block post designs.

FIG. 6A and FIG. 6B depict an exemplary pliant post design.

DETAILED DESCRIPTION

The present invention provides systems and devices for fixing the angle of instruments passing through a bone plate, as well as methods for using the same. The systems and devices include bone plates and complementary guide blocks having features for secure attachment, as well as features for simple detachment.

Definitions

It is to be understood that the figures and descriptions of the present invention have been simplified to illustrate elements that are relevant for a clear understanding of the present invention, while eliminating, for the purpose of clarity, many other elements typically found in the art. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments there between. This applies regardless of the breadth of the range.

Devices

Figure 1:
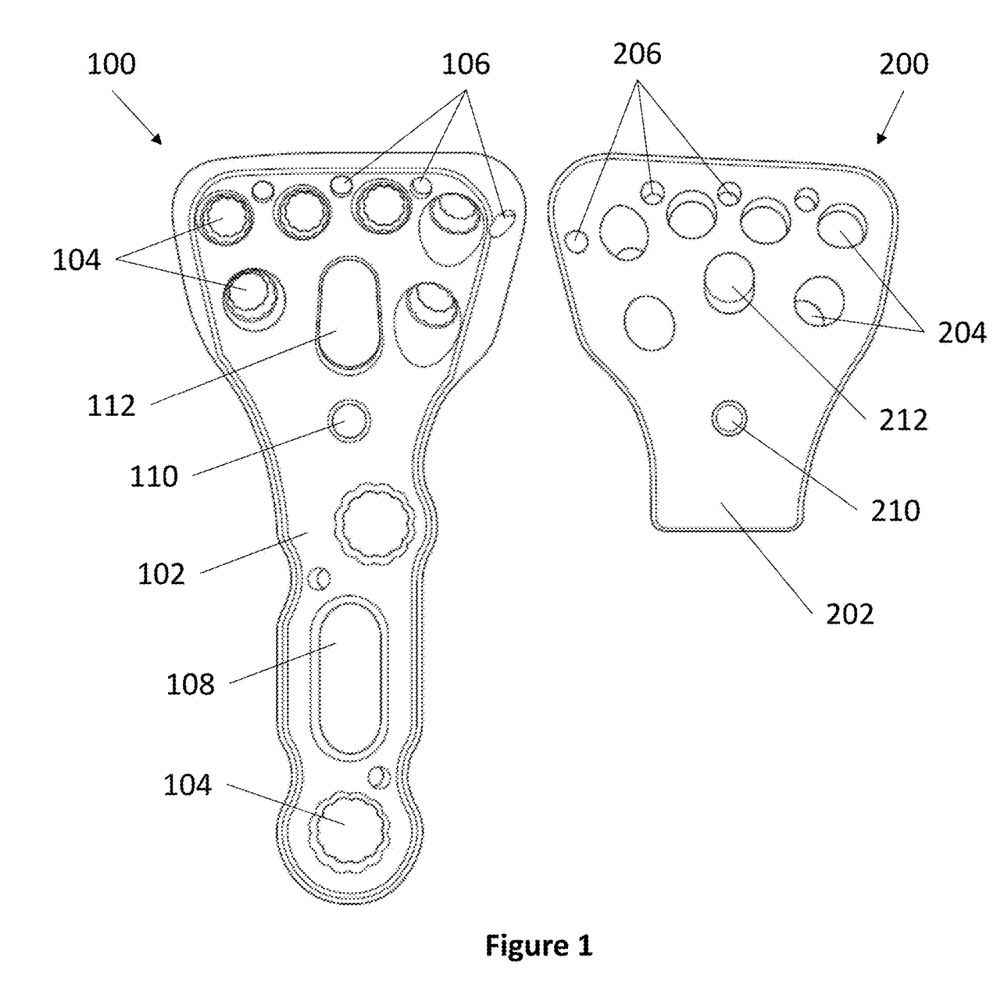
FIG. 1 depicts the top view of an exemplary bone plate and the bottom view of an exemplary complementary guide block.
Figure 2A:
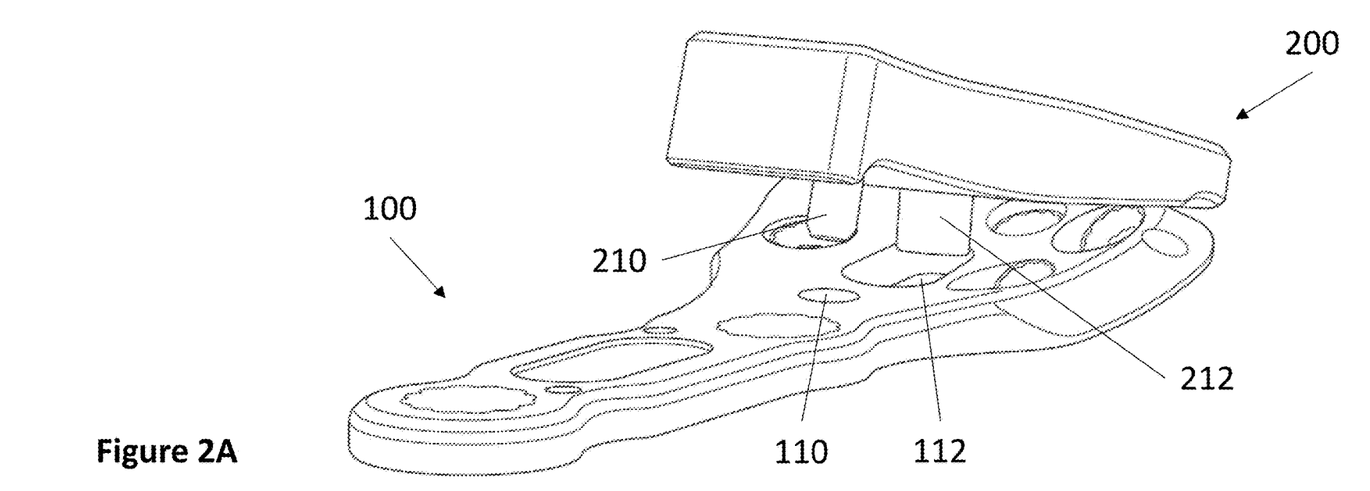
FIG. 2A and FIG. 2B depict the attachment sequence between an exemplary bone plate and an exemplary complementary guide block.
Figure 2B:
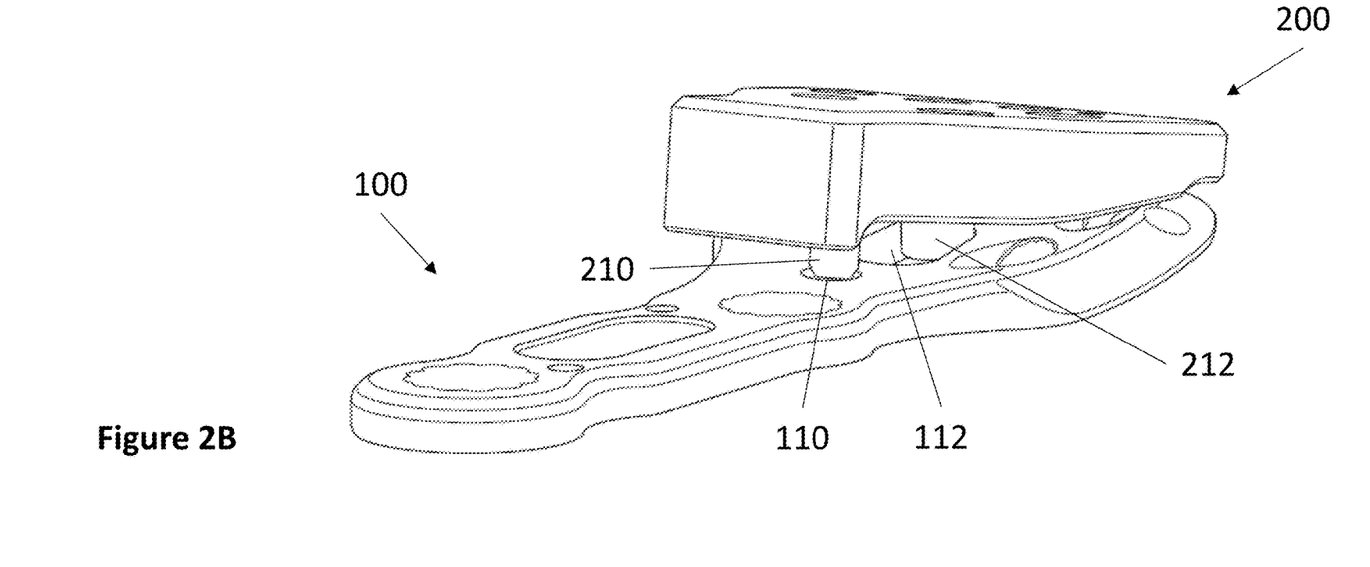

Referring now to FIG. 1, an exemplary bone plate 100 and complementary guide block 200 system is depicted. Bone plate 100 comprises plate body 102 having a plurality of bores. In some embodiments, bone plate 100 comprises large plate bores 104, small plate bores 106, elongate plate bores 108, or any combination thereof. Bone plate 100 further comprises at least one post bore, such as first post bore 110 and second post bore 112. Guide block 200 comprises guide block body 202 having a plurality of bores. In some embodiments, guide block 200 comprises large guide block bores 204, small guide block bores 206, or any combination thereof. Guide block 200 further comprises at least one post, such as first post 210 and second post 212.

Bone plate 100 facilitates the stabilization of pieces of bone and comprises features common to bone plates as understood by persons skilled in the art. Plate body 102 comprises a rigid material suitable for in vivo use, such as a polymer or a metal. In some embodiments, plate body 102 can have a uniform thickness throughout, while in other embodiments plate body 102 has a variable thickness. In some embodiments, plate body 102 is substantially flat, while in other embodiments, fixation stability is improved by a curved plate body 102 that conforms to the shape of a bone. In some embodiments, plate body 102 is at least partially bendable such that bone plate 100 can be custom fitted to the shape of a bone.

Bone plate 100 comprises a plurality of bores for inserting fasteners to secure bone plate 100 to a bone, each bore comprising an angle to fix the angle of an inserted fastener. The plurality of bores include large plate bores 104, small plate bores 106, and elongate bores 108. Large plate bores 104 are sized to accept any suitable fastener commonly used in bone fixation, such as bone screws. Typical large bore sizes commonly used in the art include diameters between 1 and 10 mm. Large plate bores 104 may be threaded or unthreaded. In some embodiments, large plate bores 104 may comprise a plurality of shapes and sizes to accommodate differently sized fasteners. Small plate bores 106 are sized to accept any suitable Kirschner wire (K-wire) or pins used in bone fixation. Typical small bore sizes commonly used in the art include diameters between 0.5 mm and 5 mm. In some embodiments, small plate bores 106 may comprise a plurality of shapes and sizes to accommodate differently sized fasteners. Elongate bores 106 may be provided for variable fastener insertion. Elongate bores 106 can have any suitable length, including ranges between 1 and 5 cm.

Bone plate 100 comprises at least one post bore for anchoring a complementary guide block 200. In some embodiments, bone plate 100 comprises a plurality of post bores, wherein each post bore can be substantially the same size or different sizes. Typical post bore sizes include diameters between 1 and 20 mm. For example, in the embodiment depicted in FIG. 1, bone plate 100 comprises a first post bore 110 and a second post bore 112, wherein the first post bore 110 has a smaller, circular shape and the second post bore 112 has a larger, oblong shape.

Figure 3:
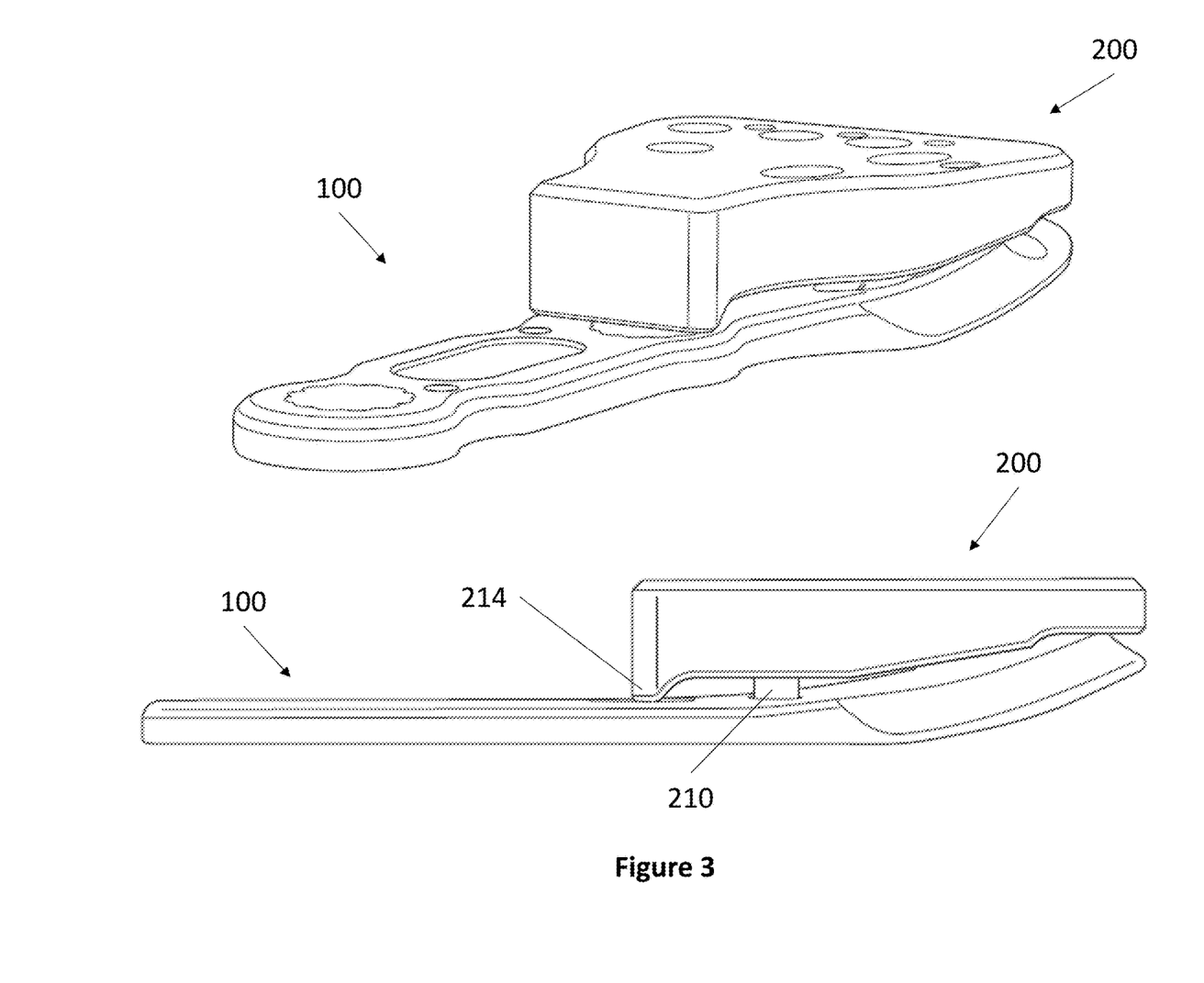
FIG. 3 depicts an exemplary complementary guide block attached to an exemplary bone plate.

Guide block 200 facilitates the drilling of pilot holes and the insertion of fasteners into a complementary bone plate 100. Guide block body 202 comprises a rigid material, such as a polymer or a metal. In some embodiments, guide block body 202 is shaped to match a complementary bone plate 100, such that when guide block 200 is secured to a complementary bone plate 100, the profiles of the two devices match when viewed from above (FIG. 3). In some embodiments, the top of guide block 200 is substantially flat. In some embodiments, the bottom of guide block 200 is contoured to match the shape of a complementary bone plate 100. In some embodiments, guide block 200 further comprises a lip 214 (FIG. 3). Lip 214 may provide a gap between guide block 200 and a complementary bone plate 100 for detaching guide block 200 from bone plate 100.

Guide block 200 comprises a plurality of bores for guiding drills and fasteners into the plurality of bores of a complementary bone plate 100. A bore on guide block 200 must substantially align with and match at least one bore on a complementary bone plate 100 in size and angle. For example, a large guide block bore 204 must substantially align with and match at least one large plate bore 104 on a corresponding bone plate 100 such that when guide block 200 is attached to bone plate 100, a fastener may be inserted through large guide block bore 204 and a large plate bore 104 with a constant angle. Likewise, a small guide block bore 206 must substantially align with and match at least one small plate bore 106 on a corresponding bone plate 100 such that when guide block 200 is attached to bone plate 100, a fastener may be inserted through small guide block bore 206 and small plate bore 106 with a constant angle.

Guide block 200 comprises at least one post for anchoring into a complementary bone plate 100. In some embodiments, guide block 200 comprises a plurality of posts, such as two or three posts, wherein each post can be substantially the same size or different sizes. For example, in the embodiment depicted in FIG. 1, guide block 200 comprises a first post 210 and a second post 212, wherein the first post 210 has a smaller, circular shape and the second post 212 has a larger, circular shape. Typical post sizes include diameters between 1 and 20 mm. In some embodiments, the at least one post comprises the same material as guide block body 202. In some embodiments, the at least one post comprises an at least partially deformable material, such as a plastic or rubber material.

Figure 4A:
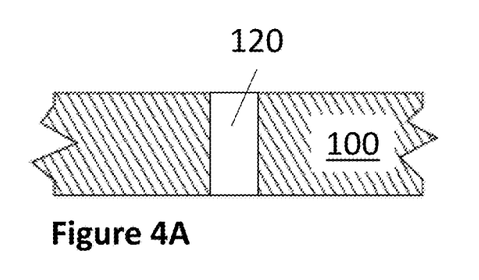
FIG. 4A depicts a straight post bore.
Figure 4B:
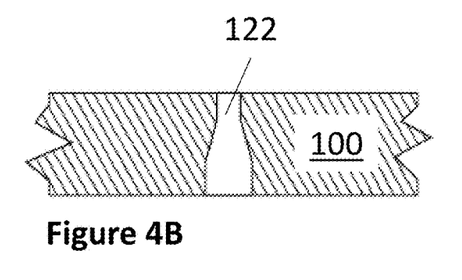
FIG. 4B depicts a flared post bore.
Figure 4C:
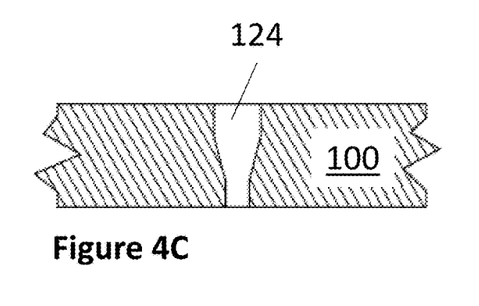
FIG. 4C depicts a tapered post bore.
Figure 4D:
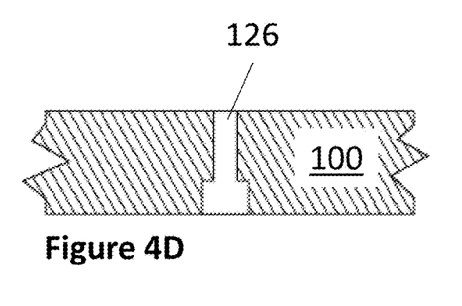
FIG. 4D depicts a stepped post bore.
Figure 4E:
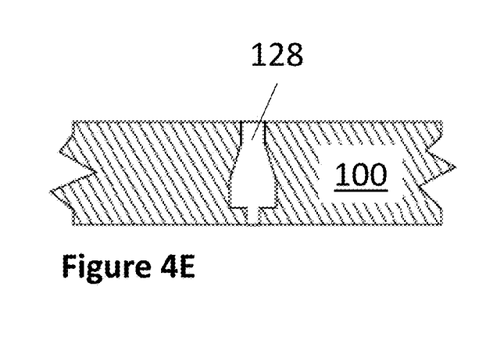
FIG. 4E depicts a recessed post bore.

The present invention provides a plurality of designs for post bores in bone plate 100 and posts on guide block 200. Post bores and posts can have any suitable cross section, such as circular, ovoid, square, rectangular, and the like. Referring now to FIG. 4A through FIG. 4E, a plurality of cutaway post bore designs for bone plate 100 are depicted. FIG. 4A depicts an exemplary straight post bore 120, wherein the post bore comprises a constant diameter throughout. FIG. 4B depicts an exemplary flared post bore 122, wherein the post bore comprises an increasing diameter from top to bottom. FIG. 4C depicts an exemplary tapered post bore 124, wherein the post bore comprises a decreasing diameter from top to bottom. FIG. 4D depicts a stepped post bore 126, wherein the post bore comprises at least two sections having different diameters. FIG. 4E depicts an exemplary recessed post bore 128, wherein the post bore comprises at least two regions, wherein at least one region has a constant diameter and at least one region has a flared or tapered diameter.

Figure 5A:
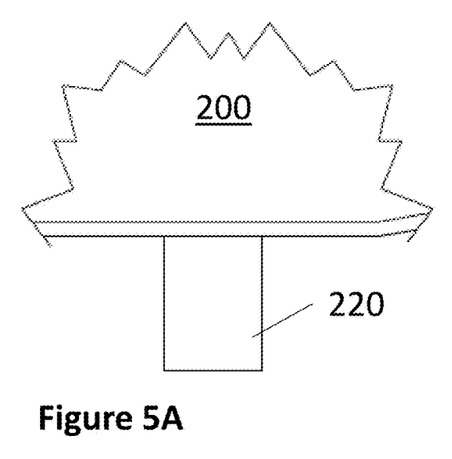
FIG. 5A depicts a straight post.
Figure 5B:
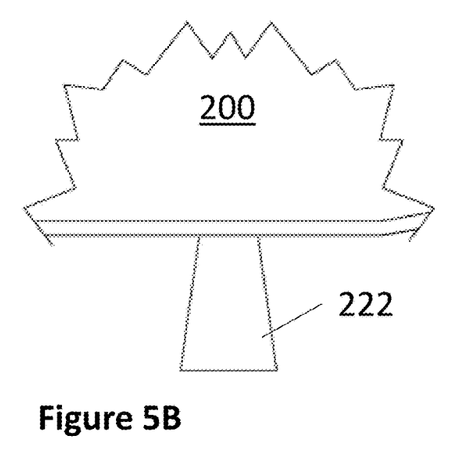
FIG. 5B depicts a flared post.
Figure 5C:
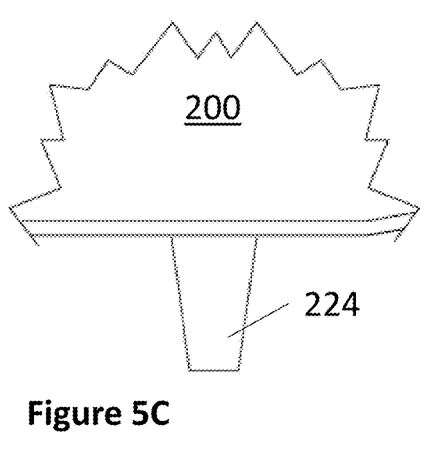
FIG. 5C depicts a tapered post.
Figure 5D:
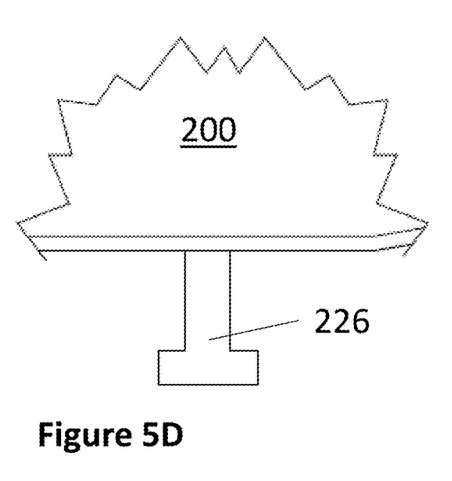
FIG. 5D depicts a stepped post.
Figure 5E:
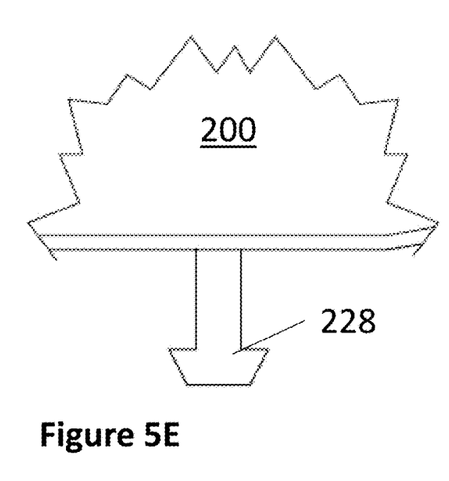
FIG. 5E depicts a barbed post.

Referring now to FIG. 5A through FIG. 5E, a plurality of side profiles for guide block 200 post designs are depicted. FIG. 5A depicts an exemplary straight post 220, wherein the post comprises a constant diameter throughout. FIG. 5B depicts an exemplary flared post 222, wherein the post comprises an increasing diameter extending away from guide block 200. FIG. 5C depicts an exemplary tapered post 224, wherein the post comprises a decreasing diameter extending away from guide block 200. FIG. 5D depicts an exemplary stepped post 226, wherein the post comprises at least two sections having different diameters. FIG. 5E depicts an exemplary barbed post 228, wherein the post comprises at least two regions, wherein at least one region has a constant diameter and at least one region has a flared or tapered diameter.

Figure 6A:
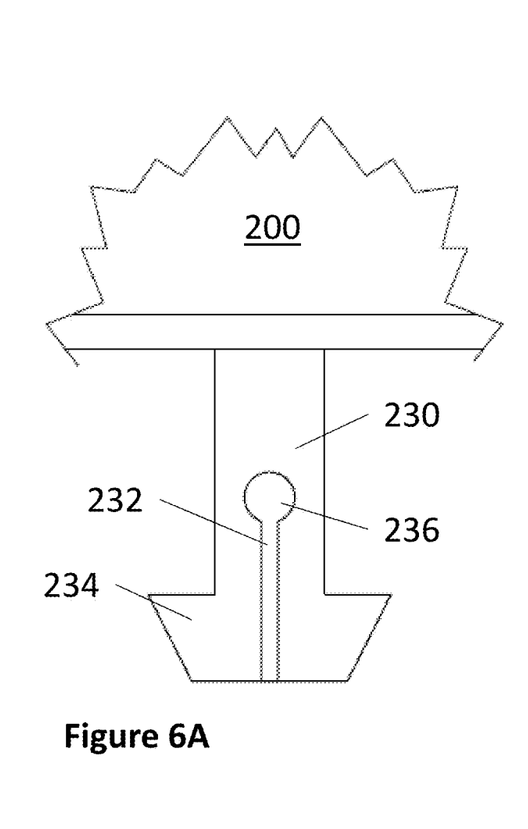
FIG. 6A is a side view of an exemplary pliant post.
Figure 6B:
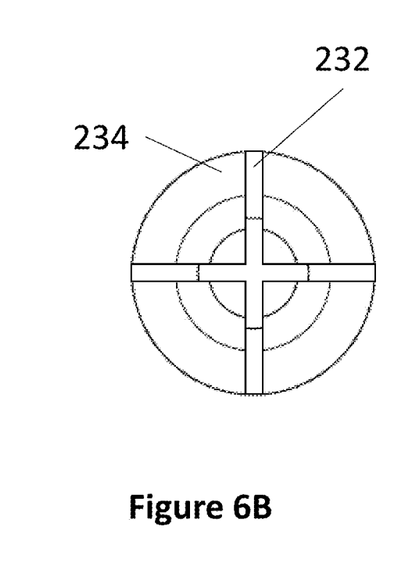
FIG. 6B is a bottom view of an exemplary pliant post.

Referring now to FIG. 6A and FIG. 6B, a pliant post 230 is depicted. Pliant post 230 comprises at least one cut 232 splitting the post, forming pliant elements 234. In some embodiments, hole 236 is provided to increase the pliability of pliant elements 234. Pliant elements 234 can reversibly deform inwards, such that pliant post 230 may enter a post bore having an opening with a smaller diameter than the non-deformed diameter of pliant post 230. Pliant elements 234 can reversibly deform outwards, such that pliant post 230 may have an effectively larger diameter than the non-deformed diameter of pliant post 230.

Figure 7:
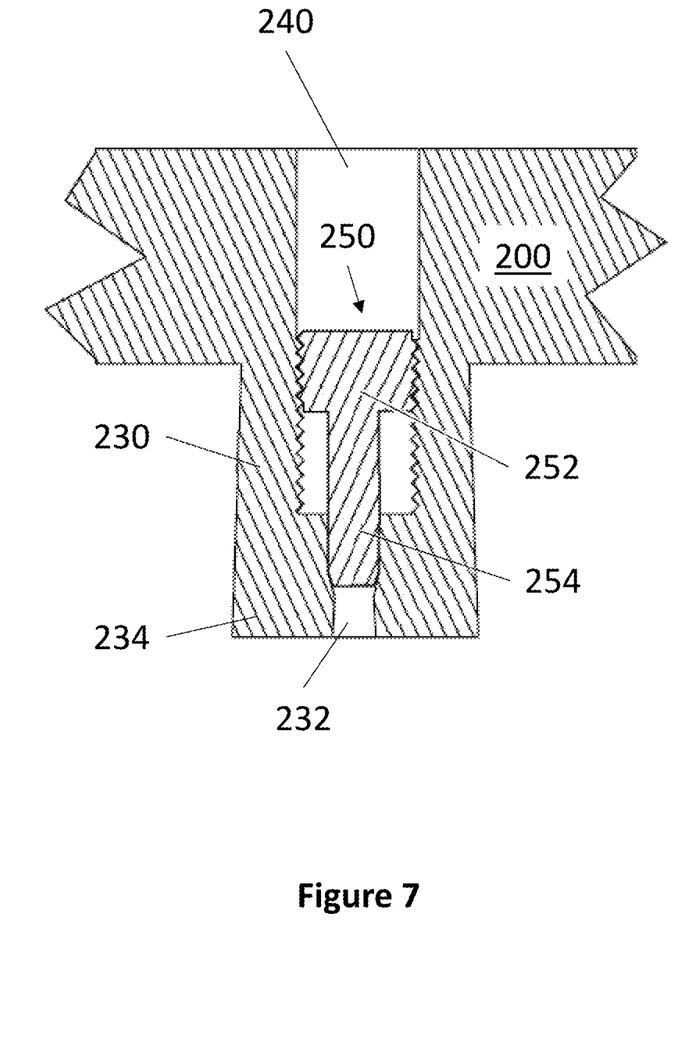
FIG. 7 depicts an exemplary pliant guide block post having an expansion mechanism.

Referring now to FIG. 7, an exemplary pliant post 230 with expansion bore 240 is depicted. Expansion bore 240 passes through guide block 200 and through the center of pliant post 230. In some embodiments, expansion bore 240 is at least partially threaded, such that a guide block screw 250 may be actuated within expansion bore 240. Guide block screw 250 comprises guide block screw head 252 and guide block screw shank 254. In some embodiments, guide block screw head 252 is threaded. Guide block screw shank 254 may be threaded or unthreaded. Actuating guide block screw head 252 in one direction advances guide block screw shank 254 through pliant post 230 and into cut 232, wherein the guide block screw shank 254 deforms pliant elements 234 outwards, effectively increasing the diameter of pliant post 230. Actuating guide block screw head 252 in the opposite direction retreats guide block screw shank 254 from cut 232, wherein pliant elements 234 return to their non-deformed state.

It should be understood that the features of pliant post 230 in FIG. 6 and the expansion mechanism in FIG. 7 are not limited to inclusion in pliant post 230. For example, features such as cut 232 and hole 236 may be introduced into any of the post designs presented herein to provide pliability to the post design. Features such as expansion bore 240 and guide block screw 250 may be introduced into any of the post designs presented herein to provide a means for reversibly expanding the effective post diameter.

Figure 8:
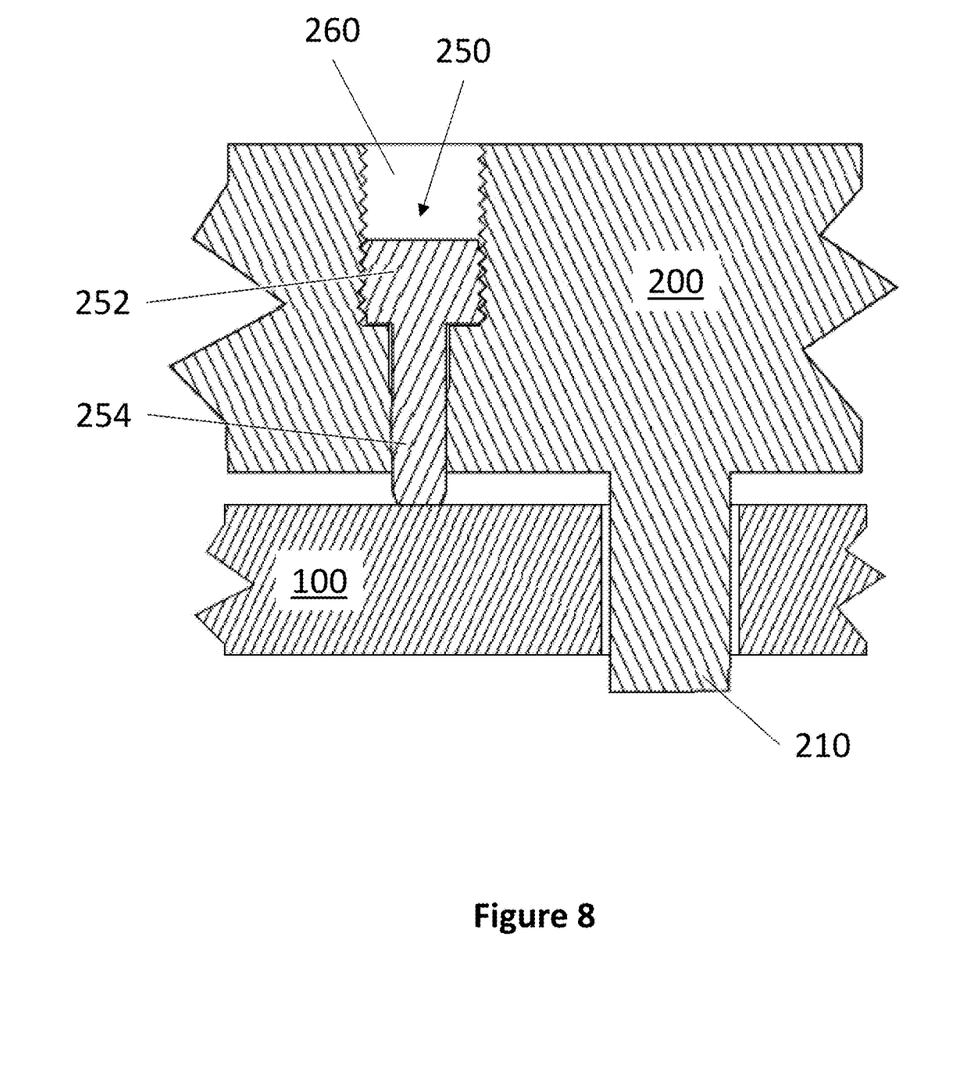
FIG. 8 depicts an exemplary guide block having a separation mechanism.

Referring now to FIG. 8, an exemplary separation mechanism is depicted. The separation mechanism comprises separation bore 260 and guide block screw 250. Separation bore 260 is at least partially threaded, such that guide block screw 250 may be actuated within separation bore 260. As previously described, guide block screw 250 comprises guide block screw head 252 and guide block screw shank 254, wherein in some embodiments guide block screw head 252 is threaded, and guide block screw shank 254 may be threaded or unthreaded. Actuating guide block screw head 252 in one direction advances guide block screw shank 254 through separation bore 260. If guide block 200 is attached to bone plate 100, the advancement of guide block screw shank 254 contacts bone plate 100, and further actuation of guide block screw 250 causes separation between guide block 200 and bone plate 100 and the extraction of post 210 from bone plate 100.

Methods of Making

The devices of the present invention can be made using any suitable method known in the art. The method of making may vary depending on the primary material used. For example, devices substantially comprising a metal may be milled from a larger block of metal or may be cast from molten metal. Likewise, devices substantially comprising a plastic or polymer may be milled from a larger block or cast. In some embodiments, the devices may be made using 3D printing techniques commonly used in the art.

Methods of Use

The present invention provides methods for attaching a guide block 200 to a bone plate 100 for guiding the drilling of pilot holes and the placement of fasteners into bone. The guide blocks and bone plates of the present invention are designed to be complementary, such that when the at least one post of a guide block 200 is seated into the complementary at least one post bore of a bone plate 100, the plurality of bores on the guide block 200 align with the plurality of bores on a bone plate 100. Seating the at least one post into the at least one post bore renders the guide block 200 firmly attached to the bone plate 100 without any lateral or rotational movement.

Seating the at least one post of a guide block 200 into the at least one post bore of a bone plate 100 may be done by pressing the post into the post bore. In certain embodiments, the posts are secured within the post bores by friction. In certain embodiments, the posts are secured within the post bores by a snap-fit. For example, a pliant post 230 may be pressed into a post bore having an opening diameter smaller than the non-deformed pliant post 230 diameter, wherein the pliant members 234 deform inwards to allow entry. After passing through the smaller opening diameter, the post bore may comprise a section having a larger diameter, wherein the pliant members 234 snap back to their non-deformed positions, securing pliant post 230 within the post bore.

In certain embodiments, the posts are secured within the post bores by expanding at least one post to increase the friction between the expanded post and the post bore. For example, a pliant post 230 having an expansion mechanism and a guide block screw 250 is amenable to the additional step of actuating the guide block screw 250 to advance guide block screw shank 254 into pliant post 230, expanding pliant members 234 outwards to engage the post bore.

With guide block 200 attached to bone plate 100 and the bores substantially aligned, any instrument may be inserted into the bores of each and into bone with a constant angle of entry. Instruments such as drill guides, drill bits, screw drivers, screw depth gauges, bone taps, and the like may be inserted with a constant trajectory.

The present invention also provides methods for detaching a guide block 200 from a bone plate 100. In some embodiments, detachment may be achieved by gripping guide block 200 and pulling it from bone plate 100. Gripping means may be provided by an operator's hands, or by an instrument such as forceps or tweezers. In other embodiments, guide block 200 may be pried from bone plate 100 by inserting an instrument between guide block 200 and bone plate 100. For example, a guide block 200 comprising lip 214 provides a gap between guide block 200 and bone plate 100, wherein an instrument may be inserted to lever the two apart.

In certain embodiments, a guide block 200 having a separation mechanism may be detached from a bone plate 100 by actuating a guide block screw 250 within separation bore 260. Guide block screw 250 is actuated to advance guide block screw shank 254 through separation bore 260 until guide block screw shank 254 contacts bone plate 100. Actuation of guide block screw 250 is continued, wherein the continued advancement of guide block screw shank 254 lifts and detaches guide block 200 away from bone plate 100.

Kits

The present invention provides a kit comprising the devices described herein for use in orthopedic procedures. In certain embodiments, the kit is a sterile packaged kit. In certain embodiments, the one or more devices of the kit are sterile and contained in one or more sterile packages within the kit. The sterile kit described herein is thus immediately ready for surgical application upon removal of the devices from their respective packages without the need for pre-operation cleaning, sterilization, or other processing. In certain aspects, the one or more devices of the kit are single-use devices. For example, in one embodiment, the one or more devices of the kit are sterile and disposable. In another embodiment, the one or more devices of the kit are repackaged after use, where, in certain embodiments, the one or more devices may be reprocessed for future use. In one embodiment, the devices may be provided in one or more blister packaging. Each blister may comprise a plastic container (e.g., PETG) component and a lid (e.g., Tyvek) component.

In certain embodiments, the kit comprises at least one bone plate, such as bone plate 100 of FIG. 1. In certain embodiments, the kit comprises at least one guide block complementary to the at least one bone plate, such as guide block 200 of FIG. 1. In certain embodiments, the kit may optionally include other instruments, such as and without limitation, one or more implantable screws, one or more implantable K-wires, one or more guide wires, one or more screw drivers, one or more screw depth gauges, one or more drill bits, one or more bone taps, and/or one or more drill guides.

In certain embodiments, the kit comprises instructional material. Instructional material may include a publication, a recording, a diagram, or any other medium of expression which can be used to communicate the usefulness of any of the devices or implant kits described herein. The instructional material may also include description of one or more steps to perform any of the methods described herein. The instructional material of the kit may, for example, be affixed to a package which contains one or more instruments which may be necessary for the desired procedure. Alternatively, the instructional material may be shipped separately from the package, or may be available electronically, such as accessible from the Internet, or any downloadable electronic document file format.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A bone plate and complementary guide block system, comprising:
   a bone plate comprising a rigid plate body having a front and a rear, at least one post bore, and a plurality of bone plate bores therein, each bone plate bore having at least one angle of orientation; and
   a guide block comprising a rigid guide block body having a front, a rear, a bottom surface, and a flat upper surface, an overhanging lip positioned at the rear of the guide block, the overhanging lip extending in an inferior direction from the upper surface, at least one post on the bottom surface, and a plurality of guide block bores therein, each guide block bore having at least one angle of orientation;
   wherein the guide block is attachable to the bone plate such that the front of the guide block is positioned at the front of the bone plate, wherein the lip elevates the rear of the guide block from the bone plate to maintain the upper surface of the guide block and the bone plate in substantially parallel alignment, wherein the at least one post seats within the at least one post bore to releasably and toollessly attach the guide block to the bone plate, and wherein the plurality of guide block bores substantially align with the plurality of bone plate bores such that a fastener may pass through each of the plurality of guide block bores and each of the plurality of bone plate bores into bone.

2. The system of claim 1, wherein the bone plate body comprises a polymer or a metal.

3. The system of claim 1, wherein the guide block body comprises a polymer or a metal.

4. The system of claim 1, wherein the at least one post comprises an at least partially deformable material.

5. The system of claim 1, wherein at least one of the plurality of bone plate bores and at least one of the plurality of guide block bores is sized to fit a bone screw.

6. The system of claim 1, wherein at least one of the plurality of bone plate bores and at least one of the plurality of guide block bores is sized to fit a Kirschner wire (K-wire).

7. The system of claim 1, wherein at least one of the plurality of bone plate bores and at least one of the plurality of guide block bores is threaded.

8. The system of claim 1, wherein the guide block lip maintains a gap between the guide block and the bone plate when the two are attached.

9. The system of claim 1, wherein the at least one post bore is selected from the group consisting of:
   a straight post bore having a constant diameter throughout;
   a flared post bore having an increasing diameter from the top of the post bore to the bottom of the post bore;
   a tapered post bore having a decreasing diameter from the top of the post bore to the bottom of the post bore;
   a stepped post bore comprising at least two sections, each section having a different diameter; and
   a recessed post bore comprising at least two regions, wherein at least one region has a constant diameter and at least one region has a flared or a tapered diameter.

10. The system of claim 1, wherein the at least one post is selected from the group consisting of:
    a straight post having a constant diameter throughout;
    a flared post having an increasing diameter extending away from the guide block;
    a tapered post having a decreasing diameter extending away from the guide block;
    a stepped post comprising at least two sections, each section having a different diameter; and
    a barbed post comprising at least two regions, wherein at least one region has a constant diameter and at least one region has a flared or a tapered diameter.

11. The system of claim 1, wherein the at least one post is a pliant post comprising at least one cut splitting the post into at least two pliant elements, wherein the at least two pliant elements are reversibly deformable inwards to decrease the diameter of the pliant post and reversibly deformable outwards to increase the diameter of the pliant post.

12. The system of claim 11, wherein the pliant post further comprises:
    an at least partially threaded expansion bore extending through the pliant post and the guide block body; and
    a guide block screw having a screw head and a screw shaft;
    wherein actuating the guide block screw within the expansion bore advances the screw shaft through the pliant post and reversibly deforms the pliant elements outwards to increase the diameter of the pliant post.

13. The system of claim 1, wherein the guide block further comprises:
    an at least partially threaded separation bore extending through the guide block body; and
    a guide block screw having a screw head and a screw shaft;
    wherein actuating the guide block screw within the separation bore advances the screw shaft through the guide block to contact and push away a bone plate attached to the guide block.

* * * * *